United States Patent [19]

Shimizu et al.

[11] Patent Number: 5,454,977
[45] Date of Patent: Oct. 3, 1995

[54] SILACYCLOHEXANE COMPOUND, A METHOD OF PREPARING IT AND A LIQUID CRYSTAL COMPOSITION CONTAINING IT

[75] Inventors: Takaaki Shimizu, Joetsu; Tsutomu Ogihara, Niigata; Takeshi Kinsho, Joetsu; Tatsushi Kaneko, Joetsu; Ryuichi Saito, Joetsu; Hideshi Kurihara, Yokohama, all of Japan

[73] Assignee: Shin-Etsu Chemical Co., Ltd., Tokyo, Japan

[21] Appl. No.: 267,027

[22] Filed: Jun. 21, 1994

[30] Foreign Application Priority Data

Jun. 23, 1993 [JP] Japan ............................ 5-176058

[51] Int. Cl.$^6$ ............ C09K 19/34; C09K 19/30; C07F 7/08; G02F 1/13
[52] U.S. Cl. ................ 252/299.61; 252/299.63; 556/406; 359/103
[58] Field of Search .............. 252/299.01, 299.61, 252/299.63; 556/406; 359/103

[56] References Cited

U.S. PATENT DOCUMENTS 4,410,570  10/1983  Kreuzer et al. .................. 428/1

FOREIGN PATENT DOCUMENTS

| | | |
|---|---|---|
| 0060335 | 10/1981 | European Pat. Off. . |
| 0459499 | 5/1991 | European Pat. Off. . |
| 0545409 | 12/1992 | European Pat. Off. . |
| 632044 | 1/1995 | European Pat. Off. . |

OTHER PUBLICATIONS

CA:86:106714 (abstract).
CA:77:88579 (Abstract).

*Primary Examiner*—Shean Wu
*Attorney, Agent, or Firm*—Townsend & Banta

[57] ABSTRACT

A silacyclohexane compound represented by the following general formula (I).

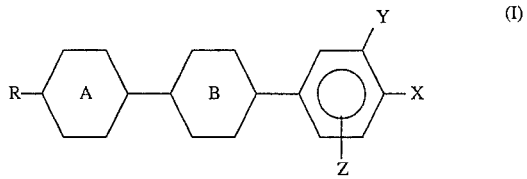

R denotes hydrogen, a linear-chain alkyl group with a carbon number of 1–10, a branched-chain alkyl group with a carbon number of 3–8, an alkoxyalkyl group with a carbon number of 2–7, or an alkenyl group with a carbon number of 2–8. For

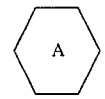

and

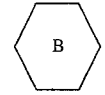

at least one of these is trans-1-silacyclohexylene or trans-4-silacyclohexylene group whose silicon at position 1 or position 4 has a substitutional group(s) of H, F, Cl or $CH_3$, and the other denotes trans-1,4-cyclohexylene group. X denotes a CN, F, Cl, $CF_3$, $CF_2Cl$, CHFCl, $OCF_3$, $OCHF_2$, $OCF_2Cl$, OCHFCl, R or OR group.

5 Claims, No Drawings

SILACYCLOHEXANE COMPOUND, A METHOD OF PREPARING IT AND A LIQUID CRYSTAL COMPOSITION CONTAINING IT

BACKGROUND OF THE INVENTION

1. Field of the invention

This invention relates to a new silacyclohexane compound, a method of preparing it, and a liquid crystal composition which contains it as well as a liquid crystal display element which contains said liquid crystal composition.

2. The Prior Art

A liquid crystal display element utilizes the optical anisotropy and dielectric anisotropy of liquid crystals. Display methods include the TN mode (twisted nematic mode), the STN mode (super twisted nematic mode), the SBE mode (super birefringence mode), the DS mode (dynamic scattering mode), the guest-host mode, the DAP mode ("deformation of aligned phase" mode) and the OMI mode (optical mode interference mode). The most common display device has a twisted nematic structure based on the Schadt-Helfrich mode.

Properties required of the liquid crystal substance used in these liquid crystal displays are somewhat different depending on the display method. However, a wide liquid crystal temperature range and stability against moisture, air, light, heat, electric fields, etc. are commonly required in all display modes. Furthermore, it is desirable for the liquid crystal material to have a low viscosity, and also to have a short address time, low threshold voltage and high contrast in the cell(s).

Currently, there is no single compound which satisfies all these requirements. In practice, liquid crystal mixtures are obtained by mixing several to more than ten liquid crystal compounds and liquid crystal like compounds. Because of this, it is also important that components of a liquid crystal composition mix easily each other.

Among liquid crystal compounds which can be components for these, one of the basic components conventionally known which control the electro-optical performance is a compound which has a so-called cyclohexyl ring-cyclohexyl ring-phenyl ring structure (CCP structure) such as

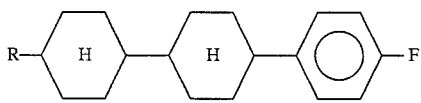

(Japanese examined patent publication (Tokko) Sho 63-13411),

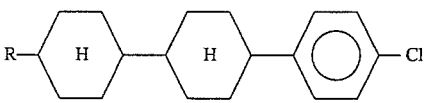

(Tokko Sho 63-32051),

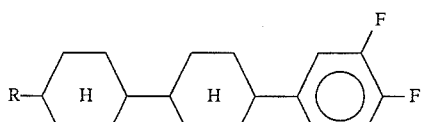

(Tokko Sho 63-44132),

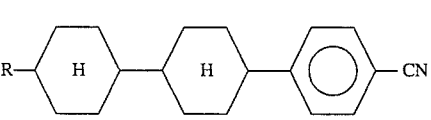

(Tokko Sho 63-46738),

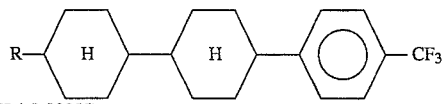

(Tokko Hei 2-29055),

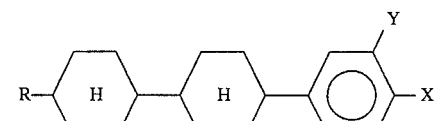

(Japanese non-examined patent publication (Tokkai) Hei 4-54138),

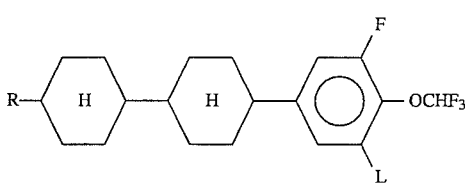

(Japanese non-examined patent publication (Tokuhyo) Hei 4-506376),

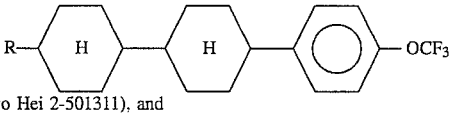

(Tokuhyo Hei 2-501311), and

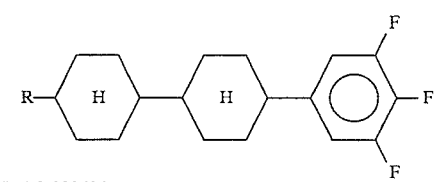

(Tokkai Hei 2-233626).

In recent years, along with the expansion of the applications of liquid crystal displays, the characteristics required of liquid crystal materials are becoming more and more advanced and demanding. In particular, superior characteristics such as a lower driving voltage, a wider temperature range for automobile onboard use and improved low temperature performance, compared with conventional liquid crystal substances, are desired.

BRIEF SUMMARY OF THE INVENTION

The object of this invention is to provide a liquid crystal compound containing silacyclohexane rings, which is completely different from the conventional liquid crystal compounds with the cyclohexyl ring-cyclohexyl ring-phenyl ring structure (CCP structure).

This invention provides a silacyclohexane compound represented by the following general formula (I).

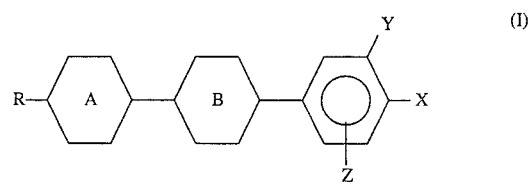

In this formula, R denotes a linear-chain alkyl group with a carbon number of 1–10, a branched-chain alkyl group with a carbon number of 3–8, an alkoxyalkyl group with a carbon number of 2–7. or an alkenyl group with a carbon number of 2–8.

For

and

at least one of these is trans-1-silacyclohexylene or trans-4-silacyclohexylene group whose silicon at position 1 or position 4 has a substitutional group of H, F, Cl or $CH_3$, and the other denotes trans-1,4-cyclohexylene group. X denotes a CN, F, Cl, $CF_3$, $CF_2Cl$, $CHFCl$, $OCF_3$, $OCHF_2$, $OCF_2Cl$, $OCHFCl$, R or OR group (R denotes a linear-chain alkyl group with a carbon number of 1–10, a branched-chain alkyl group with a carbon number of 3–8, an alkoxyalkyl group with a carbon number of 2–7, or an alkenyl group with a carbon number of 2–8). Y denotes H or F. Z denotes H or F.

This invention also provides a method of preparing the silacyclohexane compound represented by said general formula (I), characterized by the use of a reaction between an organometallic reagent R-M (M denotes MgP, ZnP or Li, and P denotes a halogen group) and a silacyclohexane compound

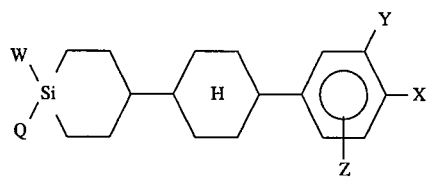

(where, W denotes a H, F, Cl or $CH_3$ group, and Q denotes a halogen or alkoxy group).

This invention also provides a method of preparing the silacyclohexane compound represented by said general formula (I), characterized by the use of a reaction between an organometallic reagent

(where,

denotes a trans-1-silacyclohexylene or trans-4-silacyclohexylene group whose silicon at position 1 or position 4 has a substitutional group of H, F, Cl or $CH_3$, or a trans-cyclohexylene group) and a silacyclohexane compound

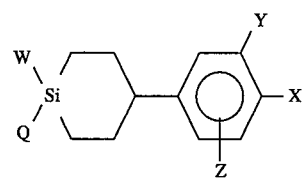

(where, W denotes a H, F, Cl or $CH_3$ group, and Q denotes a halogen or alkoxy group).

Furthermore, this invention provides a liquid crystal composition characterized by containing the compound represented by the general formula (I) as shown above, as well as a liquid crystal display element using this liquid crystal composition.

DETAILED DESCRIPTION

The new compounds represented by the general formula (I) are silacyclohexane compounds whose ring structure has at least one trans-1 or 4-silacyclohexane ring, specifically represented by ring structures shown below:

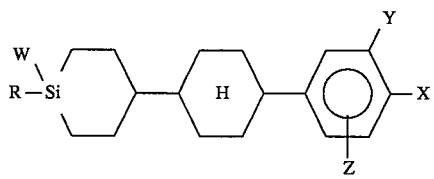

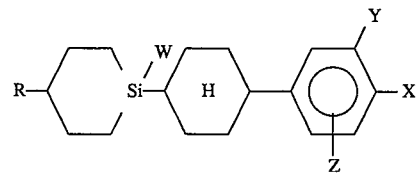

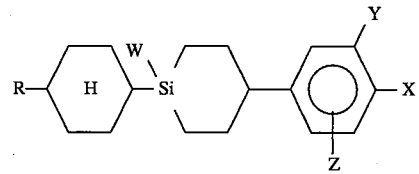

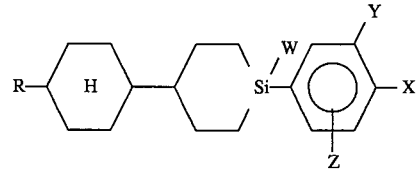

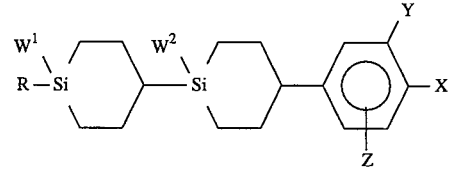

-continued

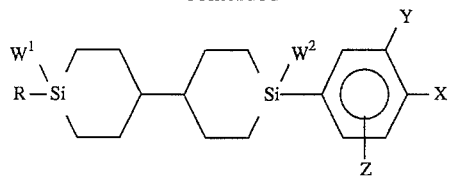

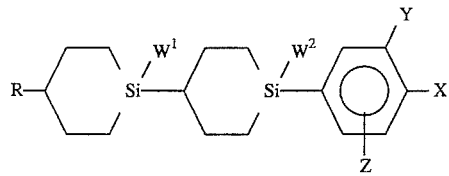

In these formulas, R denotes hydrogen, a linear-chain alkyl group with a carbon number of 1–10, i.e. a methyl, ethyl, n-propyl, n-butyl, n-pentyl, n-hexyl, n-heptyl, n-octyl, n-nonyl or n-decyl group, or a branched-chain alkyl group with a carbon number of 3–8, i.e. isopropyl, sec-butyl, iso-butyl, 1-methylbutyl, 2-methylbutyl, 3-methylbutyl, 1-methylpentyl, 2-methylpentyl, 3-methylpentyl, 1-ethylpentyl, 1-methylhexyl, 2-methylhexyl, 3-methylhexyl, 2-ethylhexyl, 3-ethylhexyl, 1-methylheptyl, 2-methylheptyl or 3-methylheptyl group, or an alkoxyalkyl group with a carbon number of 2–7, i.e. a methoxymethyl, ethoxymethyl, propoxymethyl, butoxymethyl, pentoxymethyl, hexyloxymethyl, methoxyethyl, ethoxyethyl, propoxyethyl, butoxyethyl, pentoxyethyl, methoxypropyl, ethoxypropyl, propoxypropyl, butoxypropyl, methoxybutyl, ethoxybutyl, propoxybutyl, methoxypentyl or ethoxypentyl group, or an alkenyl group with a carbon number of 2–8, i.e. a vinyl, 1-propenyl, allyl, 1-butenyl, 3-butenyl, isoprenyl, 1-pentenyl, 3-pentenyl, 4-pentenyl, dimethylallyl, 1-hexenyl, 3-hexenyl, 5-hexenyl, 1-heptenyl, 3-heptenyl, 6-heptenyl or 7-octenyl group.

$W$, $W^1$ and $W^2$, independently from each other, denote H, F, Cl or $CH_3$.

X denotes a CN, F, Cl, $CF_3$, $CF_2Cl$, CHFCl, $OCF_3$, $OCHF_2$, $OCF_2Cl$, OCHFCl, R or OR group. Y denotes H or F. Z denotes H or F.

The partial structure

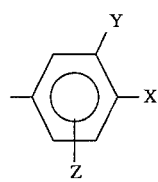

specifically denotes either of the following grous:

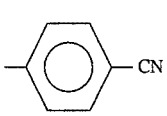

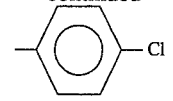

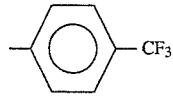

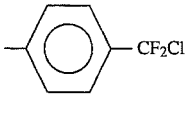

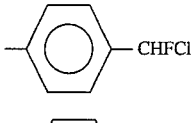

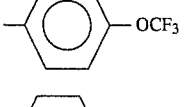

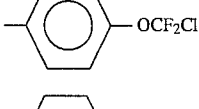

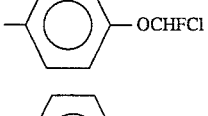

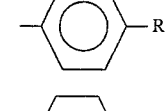

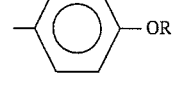

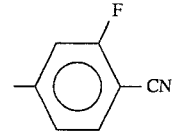

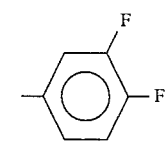

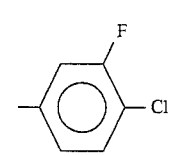

-continued
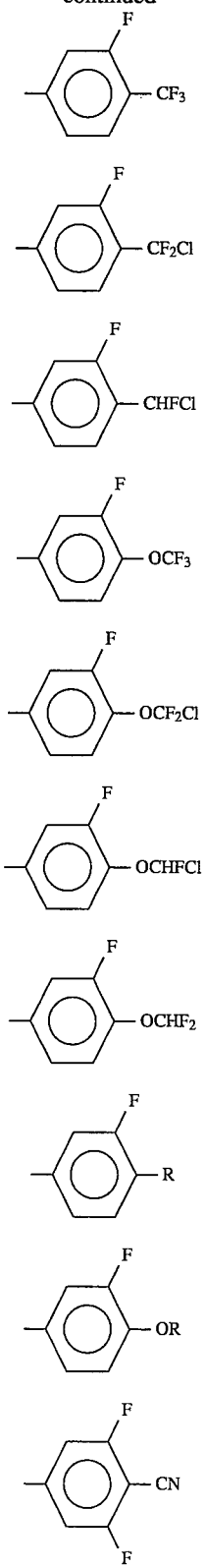
-continued
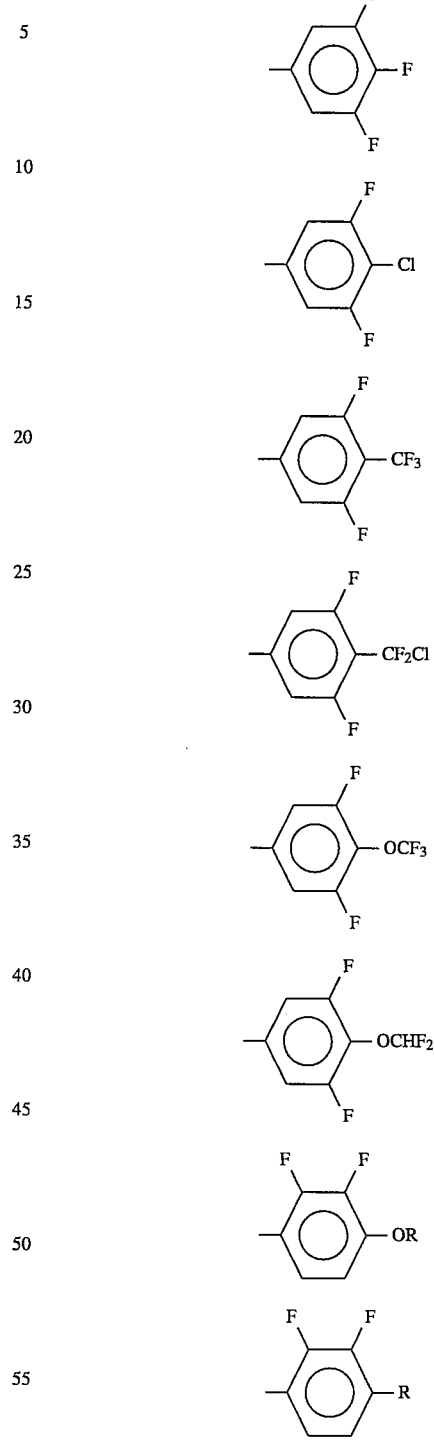
Of these, as far as the ring structure is concerned, the compounds shown below are desirable for practical use.

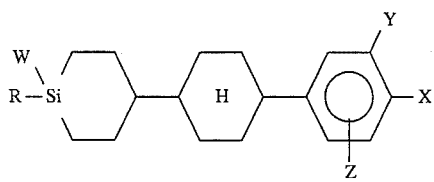

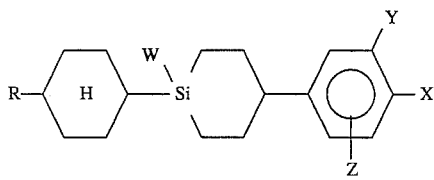

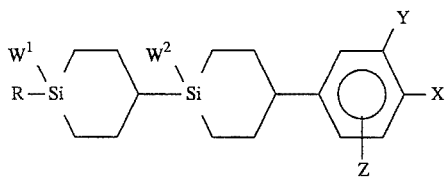

For R, the following groups are desirable for practical use: a linear-chain alkyl group with a carbon number of 2–7, i.e. an ethyl, n-propyl, n-butyl, n-pentyl, n-hexyl or n-heptyl group, or some branched-chain alkyl groups with a carbon number of 3-7 including isopropyl, 1-methylpropyl, 2-methylpropyl, 1-methylbutyl, 2-methylbutyl, 3-methylbutyl, 1-methylpentyl, 2-methylpentyl and 2-ethylhexyl groups, or an alkoxyalkyl group with a carbon number of 2-6, i.e. a methoxymethyl, methoxyethyl, methoxypropyl, methoxypentyl, ethoxymethyl, ethoxyethyl, propoxymethyl or pentoxymethyl group, or some alkenyl groups including vinyl, 1-propenyl, 3-butenyl, 1-pentenyl, 3-pentenyl, 4-pentenyl, 1-hexenyl, 5-hexenyl, 6-heptenyl and 7-octenyl groups.

H, F and CH$_3$ groups are desirable in practical use for W, W$^1$ and W$^2$.

In practical use for the partial structure

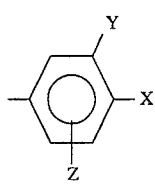

the compounds shown below are desirable.

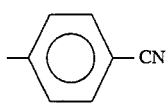

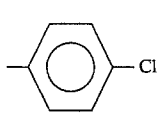

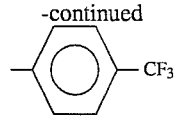

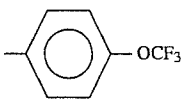

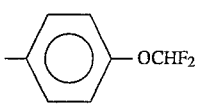

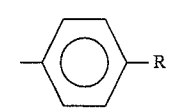

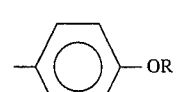

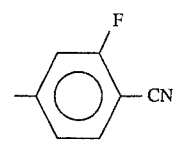

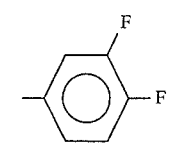

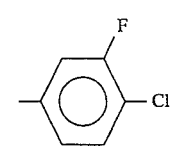

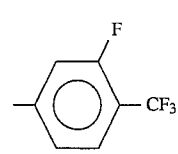

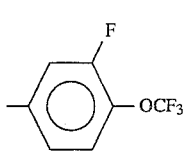

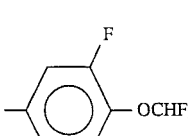

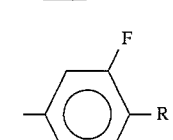

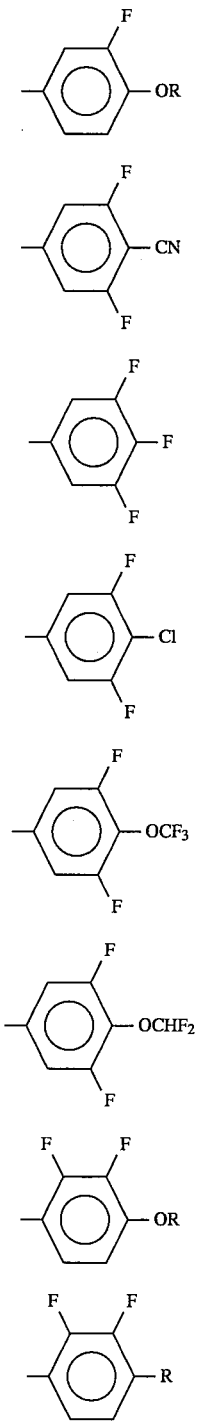

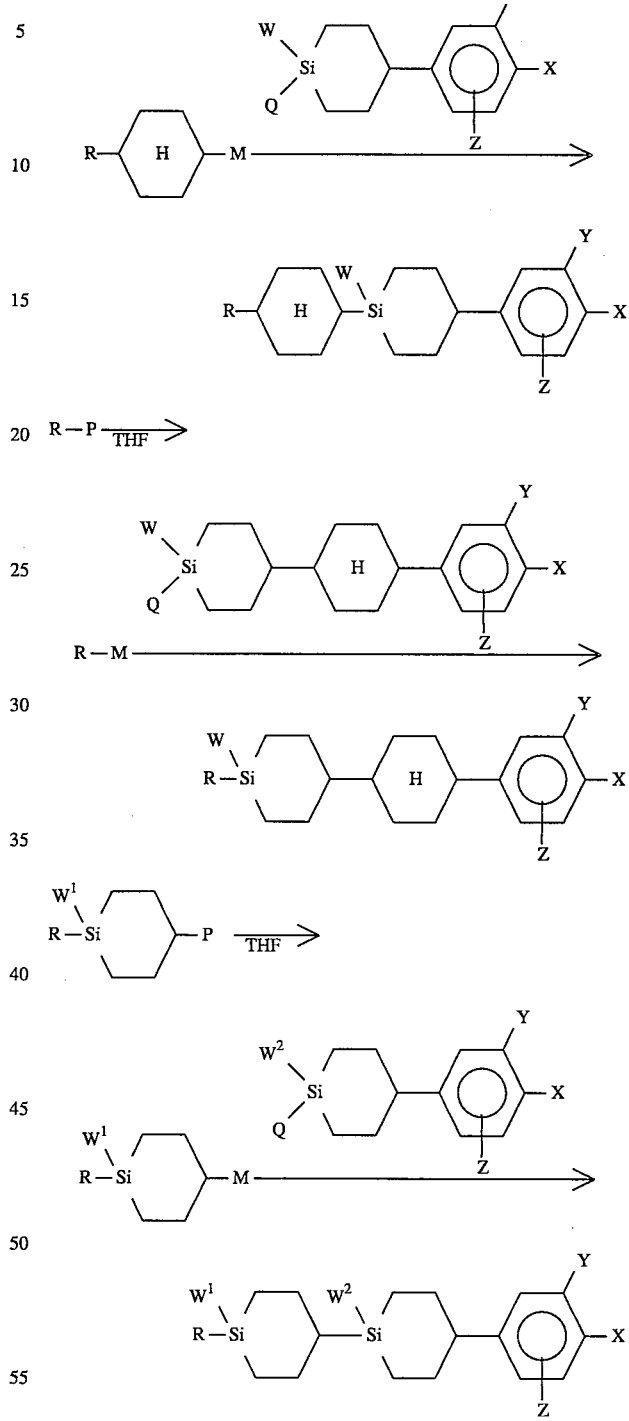

A method of preparing these compounds is described below. Although the reaction substrates are somewhat different depending on the ring structure, all of them are prepared using the organometallic coupling reactions shown below.

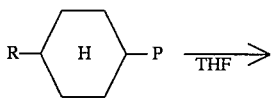

M: MgP, ZnP, Li; P: Halogen; Q: Halogen, alkoxy group. (If W=F, Cl; and W²=F, Cl, then W=Q; W²=Q; and W¹≠F, Cl)

In the preparation method described above, the organometallic reagent is prepared from the corresponding cyclohexyl halide, R-halide or silacyclohexyl halide in a solvent such as THF (tetrahydrofuran) in a conventional manner. When doing this, an appropriate metal species is chosen according to the type of the substitutional group X. The organometallic reagent thus produced is then brought into reaction with a silacyclohexane compound whose silicon has the substitutional groups W or W² and Q. The compound produced here is a mixture of trans and cis isomers in terms of the conformation of the silacyclohexane ring. A conventional purification means such as chromatography and recrystallization is employed to separate and purify the trans isomer to obtain the silacyclohexane compound of this invention represented by the general formula (I).

The silacyclohexane compound of this invention can be mixed with known compounds to obtain a liquid crystal composition. The compound used for mixing to obtain the liquid crystals compound can be chosen from among the known compounds shown below:

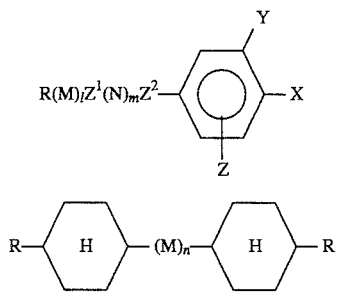

In the above formulas, (M) and (N) denote one of the following:

1) A trans-1,4-cyclohexylene group which has no substitution or which has one or more substitutional groups such as F, Cl, Br, CN or alkyl groups,
2) A ring comprising a cyclohexane ring in which O or S is substituted for one or nonadjacent two $CH_2$ groups,
3) A 1,4-cyclohexenylene group,
4) A 1,4-phenylene group which has no substitution or which has one or two substitutional groups such as F, Cl, $CH_3$ or CN groups, or
5) A ring comprising a 1,4-phenylene group in which an N atom is substituted for one or two CH groups.

$Z^1$ and $Z^2$ denote $-CH_2CH_2-$, $-CH=CH-$, $-C\equiv C-$, $-CO_2-$, $-OCO-$, $-CH_2O-$, $-OCH_2-$ or a single bond.

l, m=0, 1 or 2 (where l+m=1, 2 or 3, and n= 0, 1 or 2)

R denotes a linear-chain alkyl group with a carbon number of 1–10, a branched-chain alkyl group with a carbon number of 3–8, an alkoxyalkyl group with a carbon number of 2–7, or an alkenyl group with a carbon number of 2–8.

X, Y and Z are the same as defined for the general formula (I).

In the above description, if l or n=2, then (M) can contain heterogeneous rings, and if m=2, then (N) can contain heterogeneous rings.

The ratio of one or more types of the silacyclohexane compound of this invention contained in the liquid crystal composition is 1–50 wt %, more preferably 5–30 wt %. The liquid crystal composition can also contain a polygenetic dye(s) to generate the colored guest-host system and additives to change the dielectric anisotropy, viscosity and the orientation of the nematic phase.

The liquid crystal composition thus formed can be used to manufacture various liquid crystal display elements in conventional methods. That is, the liquid crystal composition containing the silacyclohexane compound of this invention is sealed between transparent plates which have electrodes of desired shapes and thus used as liquid crystal display elements. This element can have various undercoatings, overcoatings for the orientation control, a polarizer plate(s), a filter(s) and a reflector layer(s), as necessary. It can be made into a laminated cell or combined with other display elements. Semiconductor substrates and light sources can also be used to make various types of displays.

For the mode of the liquid crystal display element, prior-art methods in the industry of liquid crystal display elements, such as the dynamic scattering (DSM) method, the twisted nematic (TN) method, the guest-host (GH) method, the super twisted nematic (STN) method and the polymer dispersion liquid crystal (PDLC) method can be adopted.

EXAMPLES

The details of this invention is described below by referring to specific examples.

EXAMPLE 1

Preparation of 4-(trans-4-(trans-4-n-propylcyclohexyl)-4-silacyclohexyl)-1,2-difluorobenzene 4.1 g (20 mmol) of 4-n-propylcyclohexyl bromide was dropped into a mixture of 0.5 g of magnesium (21 mmol) and 50 ml of tetrahydrofuran (THF) to obtain Grignard reagent. This solution was then dropped into a 50 ml THF solution of 4.9 g (20 mmol) of 4-(4-chloro-4-silacyclohexyl)-1,2-difluorobenzene to obtain 4-(4-(trans-4-n-propylcyclohexyl)-4-silacyclohexyl)- 1, 2-difluorobenzene.

The silacyclohexane rings of this product were a mixture of trans and cis isomers. They were separated by means of chromatography to obtain 6.1 g of the trans isomer (yield 91 %).

C-N transition temperature: 28° C., N-I transition temperature: 79° C.

IR (liquid film ) $v_{max}$: 2914, 2845, 2098,1608, 1518, 1286, 1213, 812, 808 and 769 $cm^{-1}$.

The following compounds were obtained in the same manner as Example 1.

EXAMPLE 2

4-(trans-4-(trans-4-n-propylcyclohexyl)-4-silacyclohexyl)-1-fluorobenzene

C-N transition temperature: 56° C., N-I transition temperature: 111° C.

IR (KBr disc) $v_{max}$: 2914, 2843, 2102, 1605, 1508, 1225, 985, 887, 879, 812 and 710 $cm^{-1}$.

EXAMPLE 3

4-(trans-4-(trans-4-n-butylcyclohexyl)-4-silacyclohexyl)-1-fluolorobenzene

C-N transition temperature: 40%, N-I transition temperature: 107° C.

IR (KBr disc) $v_{max}$: 2920, 2846, 2102, 1605, 1508, 1225, 985, 812 and 719 $cm^{-1}$.

EXAMPLE 4

4-(trans-4-(trans-4-n-pentylcyclohexyl)-4-silacyclohexyl)-1-fluolorobenzene

This compound has characteristics shown below. The smectic phase (66°–76° C.), which was observed with a similarly structured hydrocarbon compound 4-(4-(trans-4-n-pentylcyclohexyl)-trans- 4-cyclohexyl-1-fluorobenzene, was not present for this compound.

C-N transition temperature: 55° C., N-I transition temperature: 113° C.

IR (KBr disc) $v_{max}$: 2920, 2843, 2094, 1605, 1510, 1223, 987, 887, 877, 814 and 715 cm$^{-1}$.

EXAMPLE 5

4-(trans-4-(trans-4-n-propylcyclohexyl)-4-silacyclohexyl)- 1-chlorobenzene

This compound has characteristics shown below. The smectic phase (70°–78° C.), which was observed with a similarly structured hydrocarbon compound 4-(4-(trans-4-n-propylcyclohexyl)- 4-cyclohexyl)-1-chlorobenzene, was not present for this compound.

C-N transition temperature: 48° C., N-I transition temperature: 136° C.

IR (KBr disc) $v_{max}$: 2912, 2843, 2102, 1491, 987, 877, 810, 725 and 683 cm$^{-1}$.

EXAMPLE 6

4-(trans-4-(trans-4-n-pentylcyclohexyl)-4-silacyclohexyl)- 1,2-difluorobenzene

C-N transition temperature: 45° C., N-I transition temperature: 87° C.

IR (KBr disc) $v_{max}$: 2924, 2845, 2092, 1608, 1520, 1113, 989, 891, 808, 771 and 715 cm$^{-1}$.

EXAMPLE 7

4-(trans-4-(trans-4-n-propylcyclohexyl)-4-silacyclohexyl)- 1-trifluoromethoxybenzene

EXAMPLE 8

4-(trans-4-(trans-4-n-propylcyclohexyl)-4-silacyclohexyl)- 1,2,6-trifluorobenzene

EXAMPLE 9

4-(trans-4-methyl-4-(trans-4-n-pentylcyclohexyl)- 4-silacyclohexyl)- 1-methoxybenzene

EXAMPLE 10

4-(trans-4-methyl-4-(trans-4-isobutylcyclohexyl)-4-silacyclohexyl)- 1-chloro-2,6-difluorobenzene

EXAMPLE 11

4-(trans-4-(trans-4-n-propylcyclohexyl)-4-silacyclohexyl)benzonitrile 4.1 g (20 mmol) of 4-n-propylcyclohexyl bromide was dropped into a mixture of 0.5 g of magnesium (21 mmol) and 50 ml of THF to obtain Grignard reagent. This solution was then added to a mixture of 3.0 g (22 mmol) of zinc chloride and 10 ml of THF to obtain the organozinc reagent. This reagent was then dropped into a 50 ml THF solution of 4.7 g (20 mmol) of 4-(4-chloro-4-silacyclohexyl) benzonitrile to obtain 4-( 4-(trans-4-n-propylcyclohexyl)-4-silacyclohexyl) benzonitrile. The silacyclohexane rings of this product were a mixture of trans and cis isomers. They were separated by means of chromatography to obtain 5.4 g of the trans isomer (yield 83%).

EXAMPLE 12

4-(trans-4-(trans-4-n-pentyl-4-silacyclohexyl)-4-cyclohexyl)- 1-difluoromethoxy-2,6-difluorobenzene 2.5 g (20 mmol) of n-pentyl bromide was dropped into a mixture of 0.5 g of magnesium (21 mmol) and 50 ml of THF to obtain Grignard reagent. This solution was then dropped into a 50 ml THF solution of 7.9 g (20 mmol) of 4-(4-(4-chloro- 4-silacyclohexyl)-trans-4-cyclohexyl)-1-difluoromethoxy-2,6 -difluorobenzene to obtain 4-(4-(trans-4-n-pentyl-4-silacyclohexyl)- 4-cyclohexyl)-1-difluoromethoxy-2,6-difluorobenzene. The silacyclohexane rings of this product were a mixture of trans and cis isomers. Chromatography was conducted to obtain 7.2 g of the trans isomer (yield 90%).

C-N transition temperature: 52° C., N-I transition temperature: 75° C.

IR (KBr disc) $v_{max}$: 2924, 2854, 2102, 1603, 1518, 1444, 1342, 1217, 1115, 1057, 1034, 984, 958, 887, 849 and 816 cm$^{-1}$.

The following compounds were obtained in the same manner as Example 12.

EXAMPLE 13

4- (trans-4-(trans-4-n-propyl-4-silacyclohexyl)-4-cyclohexyl)- 1-fluorobenzene

C-N transition temperature: 65° C., N-I transition temperature: 109° C.

IR (KBr disc) $v_{max}$: 2918, 2848, 2104, 1605, 1510, 1448, 1227, 985, 887, 879 and 835 cm$^{-1}$.

EXAMPLE 14

4-(trans-4-(trans-4-n-pentyl-4-silacyclohexyl)-4-cyclohexyl)- 1-fluorobenzene

This compound has characteristics shown below. The smectic phase (66°–76° C.), which was observed with a similarly structured hydrocarbon compound 4-(4-(trans-4-n-pentylcyclohexyl)-trans- 4-cyclohexyl)-1-fluorobenzene, was not present for this compound.

C-N transition temperature: 38° C., N-I transition temperature: 92° C.

IR (KBr disc) $v_{max}$: 2918, 2848, 2100, 1603, 1510, 1227, 987, 885 and 825 cm$^{-1}$.

EXAMPLE 15

4-(trans-4-(trans-4-n-propyl-4-silacyclohexyl)-4-cyclohexyl)- 1,2-difluorobenzene C-N transition temperature: 20° C., N-I transition temperature: 79° C.

IR (liquid film) $v_{max}$: 2924, 2854, 2100, 1606, 1518, 1279, 987, 887, 843 and 818 cm$^{-1}$.

EXAMPLE 16

4-(trans-4-(trans-4-n-pentyl-4-silacyclohexyl)-4-cyclohexyl)- 1,2-difluorobenzene C-N transition temperature: 14° C., N-I transition temperature: 72° C.

IR (liquid film) $v_{max}$: 2922, 2852, 2100, 1606, 1518, 1279, 1207, 987, 816 and 768 cm$^{-1}$.

EXAMPLE 17

4-(trans-4-(trans-4-n-propyl-4-silacyclohexyl)-4-cyclohexyl)-1-trifluoromethoxybenzene This compound has characteristics shown below. The smectic phase (38°–69° C.), which was observed with a similarly structured hydrocarbon compound 4-(4-(trans-4-n-propylcyclohexyl)-trans-4-cyclohexyl)-1-trifluoromethoxybenzene, was not present for this compound.
C-N transition temperature: 42° C., N-I transition temperature: 106° C.
IR (KBr disc) $v_{max}$: 2924, 2854, 2108, 1510, 1263, 1225, 1190, 1161, 985 and 845 cm$^{-1}$.

EXAMPLE 18

4-(trans-4-(trans-4-n-pentyl-4-silacyclohexyl)-4-cyclohexyl)-1-trifluoromethoxybenzene This compound has characteristics shown below. The smectic phase (52°–73° C.), which was observed with a similarly structured hydrocarbon compound 4-(4-(trans-4-n-pentylcyclohexyl)-trans-4-cyclohexyl)-1-trifluoromethoxybenzene, was not present for this compound.
C-N transition temperature: 38° C., N-I transition temperature: 80° C.
IR (KBr disc) $v_{max}$: 2924, 2854, 2102, 1510, 1267, 1223, 1194, 1159, 987 and 818 cm$^{-1}$.

EXAMPLE 19

4-(trans-4-(trans-4-n-pentyl-4-silacyclohexyl)-4-cyclohexyl)-1-chloro-2-fluorobenzene C-N transition temperature: 22.8° C., N-I transition temperature: 106.3° C.
IR (liquid film) $v_{max}$: 2922, 2852, 2100, 1485, 987, 887, 833 and 816 cm$^{-1}$.

EXAMPLE 20

4-(trans-4-(trans-4-(3-pentenyl)-4-silacyclohexyl)-4-cyclohexyl)-1-fluorobenzene

EXAMPLE 21

4-(trans-4-(trans-4-methoxypropyl-4-silacyclohexyl)-4-cyclohexyl)-1-chloro-2-fluorobenzene

EXAMPLE 22

4-(trans-4-(trans-4-n-propyl-4-silacyclohexyl)-4-cyclohexyl)-2,3-difluoro-1-ethoxybenzene C-N transition temperature: 59.3° C., S-N transition temperature: 56.7° C., N-I transition temperature: 142.5° C.
IR (KBr disc) $v_{max}$: 2926, 2854, 2092, 1514, 1475, 1300, 1115, 1078, 885, 843 and 816 cm$^{-1}$.

EXAMPLE 23

4-(trans-4-(trans-4-(3-methoxypropyl)-4-silacyclohexyl) cyclohexyl)-1,2-difluorobenzene C-N transition temperature: 37° C., N-I transition temperature: 69° C.
IR (KBr disc) $v_{max}$: 2926, 2854, 2096, 1606, 1518, 1277, 1207, 1113, 985, 887 and 814 cm$^{-1}$.

EXAMPLE 24

4-(trans-4-(trans-4-(4-pentenyl)-4-silacyclohexyl)-4-cyclohexyl)-1,2-difluorobenzene C-N transition temperature: 5° C., N-I transition temperature: 42° C.
IR (KBr disc) $v_{max}$: 2922, 2852, 2100, 1606, 1518, 1279, 1117, 887 and 818 cm$^{-1}$.

EXAMPLE 25

4-(trans-4-(trans-4-(3-methylbutyl)-4-silacyclohexyl)-4-cyclohexyl)-1,2-difluorobenzene C-N transition temperature: 38° C., N-I transition temperature: 36° C.
IR (KBr disc) p.$v_{max}$: 2922, 2852, 2100, 1608, 1518, 1279, 1207, 987, 889 and 816 cm$^{-1}$.

EXAMPLE 26

4-(trans-4-(trans-4-n-propyl-4-silacyclohexyl)-4-silacyclohexyl)-1-trifluoromethylbenzene 4.4 g (20 mmol) of 4-n-propylsilacyclohexyl bromide was dropped into a mixture of 0.5 g of magnesium (21 mmol) and 50 ml of THF to obtain Grignard reagent. This solution was then dropped into a 50 ml THF solution of 5.6 g (20 mmol) of 4-(4-chloro-4-silacyclohexyl)-1-trifluoromethylbenzene to obtain 4-(4-(4-n-propylsilacyclohexyl)-4-silacyclohexyl)-1-trifluoromethylbenzene. The silacyclohexane rings of this product were a mixture of trans and cis isomers. They were separated by means of chromatography to obtain 6.5 g of the trans-trans isomer (yield 85%).

The following compounds were obtained in the same manner as Example 26.

EXAMPLE 27

4-(trans-4-(trans-4-(3-pentenyl)-4-silacyclohexyl)-4-silacyclohexyl)-1-n-propylbenzene

EXAMPLE 28

4-(trans-4-(trans-4-methoxypropyl-4-methyl-4-silacyclohexyl)-4-silacyclohexyl)-1-trifluoromethoxy-2-fluorobenzene The compounds of this invention obtained in the examples described above were added to existing liquid crystal compositions to prepare liquid crystal compositions of this invention. For the obtained liquid crystal compositions, the threshold voltage and the transition temperature were measured.

EXAMPLE OF THE LIQUID CRYSTAL COMPOSITION

A mixture A which comprises 40 mole% of 4-(4-(trans-4-ethylcyclohexyl)-trans-4-cyclohexyl)-1,2-difluorobenzene, 35 mole % of 4-(4-(trans-4-n-propylcyclohexyl)-trans-4-cyclohexyl)- 1,2-difluorobenzene and 25 mole % of 4-(4-(trans-4-n-pentylcyclohexyl)-trans- 4-cyclohexyl)-1,2-difluorobenzene shows characteristics listed below.
C-N transition temperature: 7° C.
N-I transition temperature: 106° C.
Threshold voltage: 2.50V A mixture which comprises 85% of this mixture A and 15 mole % of 4-(trans-4-(trans-4-n-pentyl-4-silacyclohexyl)- 4 cyclohexyl)-1,2-difluorobenzene from Example 16 showed characteristics listed below.
C-N transition temperature: 2° C.
N-I transition temperature: 101° C.
Threshold voltage: 2.23V The liquid crystal compounds of this invention which have Si as a ring composing element have the following advantages over liquid crystal compounds which have a conventional CCP structure comprising similar hydrocarbon rings:

(1) Because they have the nematic liquid crystal phase extended to lower temperatures, the following low temperature characteristics improve.
(2) The viscosity in a low temperature range decreases, resulting in the improved response time in the low temperature range.
(3) Mutual solubility in a low temperature range improves.

Also, liquid crystal compounds whose X in the general formula (I) is neither R nor OR have, in addition to the advantages mentioned above, an effect of lowering the threshold voltage.

When using this invention for liquid crystal display elements, in the twisted nematic display mode, the smectic phase is not a desirable liquid crystal form, and therefore each single compound composing the liquid crystal phase should also preferably lack the smectic phase. Some of the conventional liquid crystal compounds with a CCP structure of similar hydrocarbon rings have the smectic phase. However, the liquid crystal compounds of this invention do nor have the smectic phase, and have the advantage of having the nematic phase only.

The liquid crystal compounds of this invention, depending on the selection of their substitutional groups, can be widely used as the base material which comprises the major component of the liquid crystal phase, in a manner similar to how the conventional liquid crystal compounds with a CCP structure of similar hydrocarbon rings are used. The liquid crystal compound whose substitutional group X in the general formula (I) is R or OR has near-zero dielectric anisotropy, and therefore it should preferably be used for the liquid crystal phase for display based on the dynamic scattering (DS) or deformation of aligned phase (DAP mode). The compounds in which X is other than R or OR should preferably be used for manufacturing the liquid crystal phase with a large positive dielectric anisotropy which is used in display elements based on the twisted nematic cell or the cholesteric-nematic phase transition.

We claim:

1. A silacyclohexane compound represented by the following general formula (I):

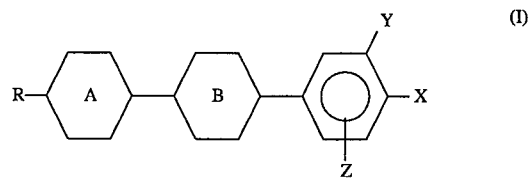

wherein R denotes hydrogen, a linear-chain alkyl group with a carbon number of 1–10, a branched-chain alkyl group with a carbon number of, 3–8, an alkoxyalkyl group with a carbon number of 2–7, or an alkenyl group with a carbon number of 2–8; and wherein at least one of

and

is trans-1-silacyclohexylene or trans-4-cyclohexylene group whose silicon at position 1 or position 4 has a substitutional group(s) of H, F, Cl or $CH_3$, and the other denotes trans-1, 4-cyclohexylene group; X denotes a CN, F, Cl, $CF_3$, $CF_2Cl$, $CHFCl$, $OCF_3$, $OCF_2Cl$, $OCHFCl$, R or OR group; Y denotes H or F, and Z denotes H or F.

2. A method of preparing the silacyclohexane compound as described in claim 1 characterized by the use of a reaction between an organometallic reagent R-M (M denotes MgP, ZnP or Li, and P denotes a halogen group) and a silacyclohexane compound

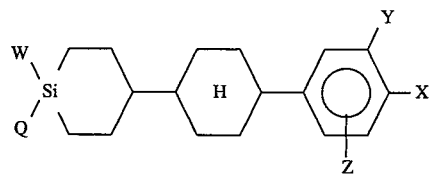

(where, W denotes a H, F, Cl or $CH_3$ group, and Q denotes a halogen or alkoxy group).

3. A method of preparing the silacyclohexane compound as described in claim 1 characterized by the use of a reaction between an organometallic reagent

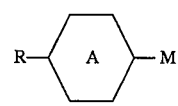

(where,

denotes a trans-1-silacyclohexylene or trans-4-silacyclohexylene group whose silicon at position 1 or position 4 has a substitutional group(s) of H, F, Cl or CH$_3$, or a cyclohexylene group) and a silacyclohexane compound

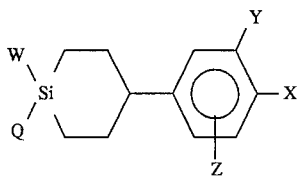

(where, W denotes a H, F, Cl or CH$_3$ group, and Q denotes a halogen or alkoxy group).

4. A liquid crystal composition characterized by containing the compound as described in claim 1.

5. A liquid crystal display element characterized by containing the liquid crystal composition as described in claim 4.

* * * * *